(12) United States Patent
Zhang et al.

(10) Patent No.: US 11,864,721 B2
(45) Date of Patent: Jan. 9, 2024

(54) ENDOSCOPE END CAP

(71) Applicants: Micro-Tech (Nanjing) Co., Ltd., Nanjing (CN); BEIJING FRIENDSHIP HOSPITAL, CAPITAL MEDICAL UNIVERSITY, Beijing (CN)

(72) Inventors: Shutian Zhang, Beijing (CN); Ming Ji, Beijing (CN); Huihong Zhai, Beijing (CN); Jianjun Shuang, Nanjing (CN); Jianyu Wei, Nanjing (CN); Derong Leng, Nanjing (CN); Changqing Li, Nanjing (CN); Zhenghua Shen, Nanjing (CN); Chunjun Liu, Nanjing (CN)

(73) Assignees: Micro-Tech (Nanjing) Co., Ltd., Nanjing (CN); Beijing Friendship Hospital, Capital Medical University, Bejing (CN)

( * ) Notice: Subject to any disclaimer, the term of this patent is extended or adjusted under 35 U.S.C. 154(b) by 587 days.

(21) Appl. No.: 16/976,007

(22) PCT Filed: Apr. 12, 2018

(86) PCT No.: PCT/CN2018/082737
§ 371 (c)(1),
(2) Date: Aug. 26, 2020

(87) PCT Pub. No.: WO2019/174091
PCT Pub. Date: Sep. 19, 2019

(65) Prior Publication Data
US 2021/0085171 A1   Mar. 25, 2021

(30) Foreign Application Priority Data
Mar. 13, 2018 (CN) .......................... 201810207220.X

(51) Int. Cl.
*A61B 1/00* (2006.01)
*A61B 1/32* (2006.01)
*A61B 1/31* (2006.01)

(52) U.S. Cl.
CPC ........ *A61B 1/00082* (2013.01); *A61B 1/0008* (2013.01); *A61B 1/0011* (2013.01);
(Continued)

(58) Field of Classification Search
CPC ............ A61B 1/00085; A61B 1/00089; A61B 1/00101
See application file for complete search history.

(56) References Cited

U.S. PATENT DOCUMENTS

| | | | | |
|---|---|---|---|---|
| 4,608,965 A | * | 9/1986 | Anspach, Jr. ...... | A61B 17/0281 600/101 |
| 4,995,868 A | * | 2/1991 | Brazier ................ | A61M 25/04 604/105 |

(Continued)

FOREIGN PATENT DOCUMENTS

| | | |
|---|---|---|
| CN | 1897868 A | 1/2007 |
| CN | 102123652 A | 7/2011 |

(Continued)

OTHER PUBLICATIONS

International Search Report dated Dec. 6, 2018, for corresponding International Patent Application No. PCT/CN2018/082737, filed Apr. 12, 2018.

(Continued)

*Primary Examiner* — Matthew J Kasztejna
(74) *Attorney, Agent, or Firm* — Westman, Champlin & Koehler, P.A

(57) ABSTRACT

An endoscope end cap, including a sleeve member, protrusion elements, and a movable sleeve. The sleeve member is connected to the front end of an endoscope, the sleeve (Continued)

member, the protrusion elements, and the movable sleeve are connected in sequence, and the movable sleeve can move freely on the outer surface of the endoscope. When the endoscope is inserted for examination, the end cap is easy to enter and does not scratch the digestive tract since the end cap has a cylinder-like structure which is smooth and has no angularity; when the endoscope is being withdrawn, the movable sleeve moves distally and abuts against the sleeve member, so as to support the protrusion elements to enable the protrusion elements to dilate the inner wall of the intestine, improving the quality of single endoscope examination, and reducing discomfort of a patient, operation risk, and operation time.

12 Claims, 11 Drawing Sheets

(52) U.S. Cl.
CPC ...... *A61B 1/00085* (2013.01); *A61B 1/00089* (2013.01); *A61B 1/00137* (2013.01); *A61B 1/32* (2013.01); *A61B 1/00101* (2013.01); *A61B 1/31* (2013.01)

(56) References Cited

U.S. PATENT DOCUMENTS

| | | | | |
|---|---|---|---|---|
| 5,421,832 | A * | 6/1995 | Lefebvre | B29C 61/0608 264/DIG. 48 |
| 6,855,126 | B2 * | 2/2005 | Flinchbaugh | A61M 39/10 604/537 |
| 8,142,348 | B2 * | 3/2012 | Miyoshi | A61B 1/00082 600/114 |
| 9,173,546 | B2 | 11/2015 | Kuhns et al. | |
| 9,808,142 | B2 | 11/2017 | Axon et al. | |
| 10,052,014 | B2 | 8/2018 | Terliuc et al. | |
| 2007/0149845 | A1 | 6/2007 | Kuhns et al. | |
| 2007/0208299 | A1 | 9/2007 | Breedveld | |
| 2011/0009696 | A1 | 1/2011 | Miyoshi | |
| 2011/0144440 | A1 * | 6/2011 | Cropper | A61B 17/3421 600/203 |
| 2011/0306833 | A1 | 12/2011 | Saadat et al. | |
| 2013/0023920 | A1 | 1/2013 | Terliuc et al. | |
| 2013/0090527 | A1 | 4/2013 | Axon | |
| 2015/0157192 | A1 | 6/2015 | Piskun et al. | |
| 2017/0112365 | A1 | 4/2017 | Ostrovsky et al. | |
| 2018/0008128 | A1 | 1/2018 | Axon et al. | |
| 2018/0168437 | A1 * | 6/2018 | Schreiner | A61B 1/00148 |
| 2020/0178773 | A1 * | 6/2020 | Miller | A61B 1/0676 |

FOREIGN PATENT DOCUMENTS

| | | |
|---|---|---|
| CN | 102905608 A | 1/2013 |
| CN | 103281971 A | 9/2013 |
| CN | 105101860 A | 11/2015 |
| CN | 105705072 A | 6/2016 |
| CN | 106343941 A | 1/2017 |
| CN | 208784696 U | 4/2019 |
| GB | 2478081 B8 | 1/2012 |
| IN | 105125158 A | 12/2015 |
| JP | 2009-532078 | 9/2009 |
| JP | 2010-178966 | 8/2010 |
| JP | 2013-529958 | 7/2013 |
| JP | 2016-507303 | 3/2016 |
| WO | 20050448828 A1 | 6/2005 |
| WO | 2011111040 A2 | 9/2011 |
| WO | 2011148172 A3 | 12/2011 |
| WO | 2014/123563 A1 | 8/2014 |
| WO | 2014123563 A1 | 8/2014 |
| WO | 2014200737 A1 | 12/2014 |
| WO | 2016130442 A1 | 8/2016 |
| WO | 2016/185358 A1 | 11/2016 |
| WO | 2016/210306 A1 | 12/2016 |
| WO | 2017068404 A1 | 4/2017 |

OTHER PUBLICATIONS

Written Opinion of the International Searching Authority dated Dec. 6, 2018, for corresponding International Patent Application No. PCT/CN2018/082737, filed Apr. 12, 2018.
Examination Report No. 1 from AU Application No. 2018413522, dated Nov. 24, 2020, 4 pages.
First Office Action from CA Application No. 3,091,868, dated Sep. 14, 2021, 5 pages.
Communication from EU Application No. 18 910 025.8, dated May 10, 2021, 6 pages.
Office Action from JP Application No. 2020-546968, dated Oct. 6, 2021, 6 pages; English translation 5 pages.
Second Office Action from CA Application No. 3,091,868, dated Jul. 28, 2022, 3 pages.
Second Communication from EU Application No. 18 910 025.8 dated Oct. 7, 2022, 4 pages.
Notice of Acceptance for AU Application No. 2018413522, dated May 20, 2021, 3 pages.
Decision of Refusal for JP Application No. 2020-546968, dated Feb. 2, 2022, 8 pages; English translation 7 pages.
Translation of the Written Opinion for International Application No. PCT/CN2018/082737, dated Dec. 13, 2018, 4 pages.
European Search Report for corresponding EP application No. 18910025.8-1126 / 3766404, dated Mar. 15, 2021.
First Office Action from CN Priority Application No. CN201810207220. X, dated Aug. 23, 2023, 6 pages.
Search Report from CN Priority Application No. CN201810207220. X, dated Aug. 15, 2023, 3 pages.

* cited by examiner

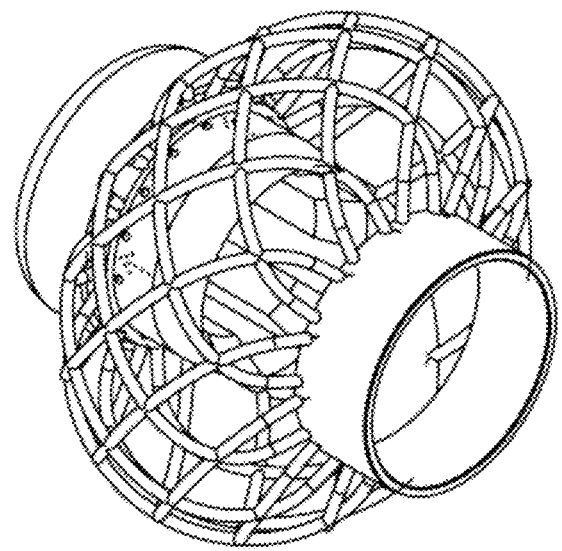
FIG. 19
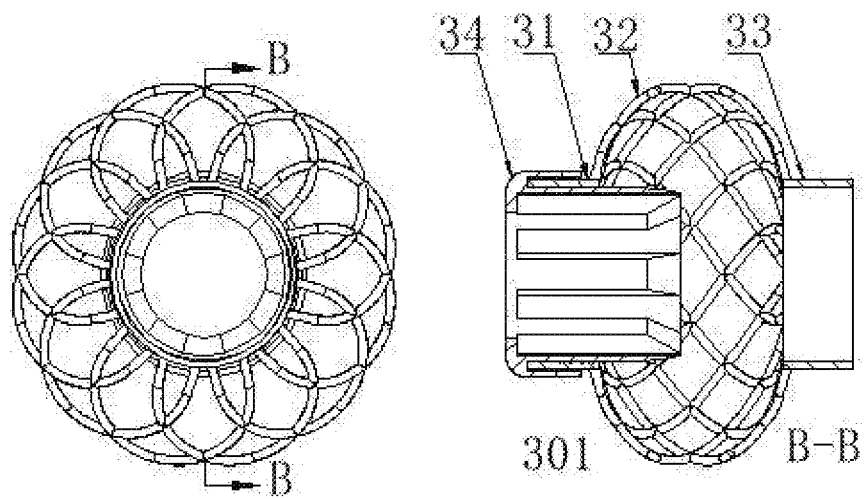
FIG. 20A
FIG. 20B

ENDOSCOPE END CAP

CROSS-REFERENCE TO RELATED APPLICATION

This Application is a Section 371 National Stage Application of International Application No. PCT/CN2018/082737, filed Apr. 12, 2018 and published as WO 2019/174091 A1 on Sep. 19, 2019, not in English, the contents of which are hereby incorporated by reference in their entirety.

TECHNICAL FIELD

The present disclosure relates to a device for medical endoscopy, and in particular to an endoscopic end cap (endoscope end cap).

BACKGROUND ART

In endoscopy procedures, flexible instruments are used to view a body lumen, such as the gastrointestinal tract and many others. The instruments are provided with fibre-optic or charge-couple device (CCD) cameras, which enable images to be transmitted around bends and images to be produced and displayed on a screen. Enteroscopy is the endoscopy of the small intestine and colonoscopy is the endoscopy of the colon and the distal part of the small intestine. Colonoscopy and enteroscopy are the most effective techniques to assess the state of health of the bowel.

Colorectal adenoma (especially villous adenoma) is the main precancerous disease of colorectal cancer (CRC). Timely screening and discovery and endoscopic resection of colorectal adenoma is the most effective measure for preventing CRC. At present, colonoscopy is generally recognized as the "gold standard" for the detection of colorectal cancer and its precancerous lesions, namely adenoma.

However, there are some objective factors, particularly the special physiological structure of the intestinal tract itself. The intestinal tract itself is convoluted in many places. Further, the colon has three major physiological characteristics including teniae coli, haustra, and epiploic appendage. Some of the walls of the colon are contracted into many sac-shaped pouches, i.e., haustra, and there are many epiploic appendages near the teniae coli. The outside of the epiploic appendages is surrounded by the peritoneum. Sometimes epiploic appendages containing too much fat may be twisted or even fall into the intestine, causing intussusception. Therefore, the lumen of the colon is not smooth and flat, but there are many ring-shaped folds, and solid feces or liquid feces in the colonic lumen. Moreover, due to the adenoma characteristics (such as size, shape, number, colorectal anatomic site, etc.), an intestinal adenoma is probably undetected during colonoscopy of the presence or absence of an intestinal adenoma. For example, during examination by a colonoscope which is being withdrawn or retracted, the soft intestinal wall may be close to the lenses of the colonoscope to disturb the imaging, and some small adenomas that exist under the ring-shaped folds or solid feces or liquid feces in the colonic lumen may be undetected. During the withdrawal of the colonoscope, "jerks" and "rapid slippages" of the colonoscope may occur in the colonic lumen, which further increases the proportion of undetected cases. Therefore, colonoscopy has not been performed with satisfactory quality.

Colorectal cancer is the second leading cause of cancer death behind lung cancer in Europe and North America. The incidence of colorectal cancer in China also tends to increase year by year. Colonoscopy is the gold standard for bowel examination and is the most effective way to prevent the incidence of colorectal cancer. However, at present, colonoscopy is not highly popularized in China and each examination is performed within a limited time, thus there are probably undetected cases, and it is not possible to achieve early detection, early treatment, and early prevention. As a result, the incidence of colorectal cancer in China is much higher than those in developed countries such as Japan. Medical staff should pay attention to this issue.

During colonoscopy for early cancer screening, if the discovered polyps and adenomas are resected in time, the risk of developing them into cancer can be greatly reduced, and the incidence of colorectal cancer can be reduced. Therefore, it is recommended in western developed countries that people over the age of 50 should be subjected to a colonoscopy every two years. However, due to the special structures of the rectum and colon consisting of many bends and inner wall folds, the back of the folded walls is objectively invisible from the viewing angle in the traditional colonoscopy and thus some cases may be undetected. Reports show that adenomas are detected by different colonoscopists at a rate varying from 7% to 53%. There is still much room for increase in the adenoma detection rate.

PCT Patent Publication No. WO2011/148172 describes a covering for a medical endoscopic instrument, which is a covering having a plurality of moveable, external angled projecting elements, wherein the projecting elements are similar to brush head bristles. When the endoscope is advanced, the projecting elements are tilted toward the surface of the endoscope. When the endoscope is being withdrawn, the bristles are splayed to help stretch the folds, so that the colonoscopy is carried out in a better manner. However, the brush head bristles apply a limited support force to the lumen, thus the field of view of the endoscope cannot be enlarged well.

PCT Patent Publication No. WO2014/123563 describes an endoscopic sleeve including a tubular member and spaced projecting elements, wherein the projecting elements are bendable towards both proximal and distal directions of the tubular member. Because the projecting elements are bendable only to a limited degree, a greater resistance may be applied when the endoscope is being advanced through some curved parts of the intestinal tract. In addition, it is difficult to effectively open the folds in the intestinal tract at some parts with colon intussusception and teniae coli.

Therefore, there is an urgent need for an end cap that can overcome the above-mentioned related problems occurring during colonoscopy, increase the detection rate of diseases by colonoscopy, and also shorten the endoscope withdrawal time.

SUMMARY

An object of the present disclosure is to design an endoscopic end cap. Especially when used in cooperation with a colonoscopy, the endoscopic end cap provides less resistance to insertion of the colonoscope, and also enlarges the space occupied by the colonoscope in the lumen and stretches the shortened and folded intestinal lumen during examination accompanied by colonoscope withdrawal, so that the folded and curved parts of the intestinal tract can be visualized at the lenses of the colonoscope to the greatest extent, thereby enlarging the range visible by the colonoscope, shortening the time for examination accompanied by colonoscope withdrawal, improving the quality of a single colonoscopy, reducing discomfort of a patient, operational risks and time costs, and thus preventing and reducing the incidence of colorectal cancer.

The endoscopic end cap of the present disclosure comprises a sleeve member, a projecting element, and a movable sleeve. The sleeve member is made of an elastic material and is elastically deformable, and is expanded to cover an end of an endoscope and be tightly matched with the outer diameter of the endoscope, so as to ensure no detachment or slip-off of the end cap when entering or exiting a lumen of a human body. The projecting element surrounds the sleeve member. When normally dilated, the projecting element may support and dilate the lumen of the human body or open an inner wall of a natural lumen, and drag the back portion of the folded wall of the intestinal tract out, so that it is visualized within the field of view of the endoscope, whereby the detection rate in endoscopy will be greatly increased. The movable sleeve is located at the proximal end of the end cap, has an inner diameter slightly larger than that of the sleeve member, and is movable forward and backward in the axial direction of the endoscope with a varying force exerted thereon.

When the endoscope is being inserted into a human body for endoscopy, the movable sleeve moves proximally in the axial direction of the endoscope, and the projecting element is pulled by the movable sleeve to extend proximally. In this case, the projecting element is stretched in the axial direction of the endoscope and is in a radially contracted state with a smaller outer perimeter, thus less resistance is exerted thereon, which facilitates the introduction of the endoscope into the patient's body. When the endoscope is being removed, i.e., withdrawn, from the human body, the movable sleeve is pressed by human tissue and moves distally in the axial direction of the endoscope, so that the projecting element is normally dilated and restored to the original state, so as to dilate the inner wall of the digestive tract of the patient. In this case, the projecting element is compressed along the axial direction of the endoscope and is in a radially dilated state with a larger outer perimeter, thus a greater resistance is exerted thereon. Because the digestive tract is dilated, the range of the field of view of the endoscope is enlarged, and thus the endoscopic detection rate will be increased, and the proportion of cases undetected by endoscopy will be greatly reduced. Moreover, the projecting element is in direct contact with the inner wall of the digestive tract, thus lesions or polyps on the folds behind the inner wall of the digestive tract are dragged out as the endoscope is being withdrawn, so that it is only necessary for the endoscopist to inject a small amount of gas to assist in the observation during examination, which can reduce the patient's pain.

Therefore, during the entire withdrawal movement of the endoscope, the colonic lumen is enlarged, and the curved parts of the colon will be straightened and the folded parts of the colon will be flattened by a friction force from the endoscopic end cap, so that some adenomas hidden in the curved parts or folded parts of the colon or under the excrement are exposed to the field of view of the endoscope, whereby the effect of the endoscopy is improved, and the endoscope withdrawal time is advantageously reduced.

BRIEF DESCRIPTION OF DRAWINGS

FIG. 19 is a schematic view of a mesh-type endoscopic end cap combined with an end cap cover.

FIGS. 20A and 20B are a left side view and a front view of the mesh-type endoscopic end cap combined with an end cap cover shown in FIG. 19, respectively.

Figure 1:
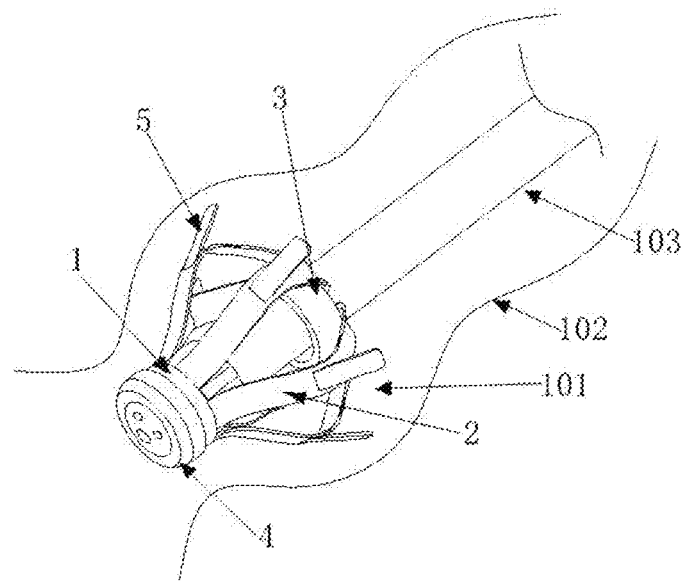
FIG. 1 is a schematic view of an endoscopic end cap during withdrawal of an endoscope, assembled with the endoscopic end cap, from a body lumen.

DESCRIPTION OF REFERENCE SIGNS 1, 21, 31, sleeve member; 2, 22, 32, projecting element (protrusion element); 3, 23, 33, movable sleeve; 5, fin; 4, 24, 34, end cap cover; 25, umbrella-shaped projecting element; 26, connecting rod; 101, 201, 301, endoscopic end cap; 102, body lumen; 103, endoscopic shaft; 7, protrusion.

DETAILED DESCRIPTION OF EMBODIMENTS

The technical solution of the present disclosure will be described in detail below with reference to the drawings. It should be understood that the specific embodiments described herein are intended only to explain the present disclosure and are not intended to limit the present disclosure. The scope of the present disclosure is not limited by these embodiments, but is determined by the scope of the patent application. In order to provide a clearer description and enable those skilled in the art to understand the description of the present disclosure, the portions in the drawings are not necessarily drawn according to their relative dimensions, the ratios of some dimensions to other related scales will be highlighted and exaggerated, and irrelevant or unimportant details are not fully drawn for simplicity in drawings.

FIG. 1 schematically illustrates an endoscopic end cap 101, constructed and operated in accordance with an embodiment of the present disclosure, which is mounted on an endoscopic shaft 103 and inserted in a body lumen 102, including, but not limited to, the colon or other parts of the gastrointestinal tract or other body lumens. An endoscope has one or more image capturing devices for viewing the body lumen and working channels, as is well known in the art. The distal end of the endoscopic end cap 101 is the end portion which is commensurate with the end of the endoscopic shaft 103. It is the end portion which is furthest from the endoscopist/colonoscopist and as such is the end portion of the instrument which is deepest within the patient's body. A distal movement of the endoscope is an insertion of the endoscope, i.e., further into a patient's body lumen, and a proximal movement of the endoscope is a withdrawal of the endoscope towards the operator.

In a non-limiting embodiment of the present disclosure, the endoscopic end cap 101 comprises a sleeve member 1, a projecting element 2, and a movable sleeve 3, wherein the sleeve member 1 has an inner diameter smaller than that of the endoscopic shaft and may be expanded to cover the distal end of the endoscopic shaft and be tightly matched with the endoscopic shaft 103, to ensure no detachment or slip-off of the endoscopic end cap 101 when entering or exiting a lumen of a human body. The sleeve member 1 may have a shape selected from a truncated pyramid, a cone, and a cylindrical shape, and may have a cross-sectional shape selected from a circle, an ellipse, a triangle, a polygon, and the like. The projecting element 2 is connected to the sleeve member 1 at one end thereof and connected to the movable sleeve 3 at the other end thereof. The movable sleeve 3 is located at the proximal end of the projecting element 2 and has an inner diameter slightly larger than the inner diameter of the sleeve member 1, so as to ensure its free forward or backward movement in the axial direction around the periphery of the endoscopic shaft.

Figure 2A:
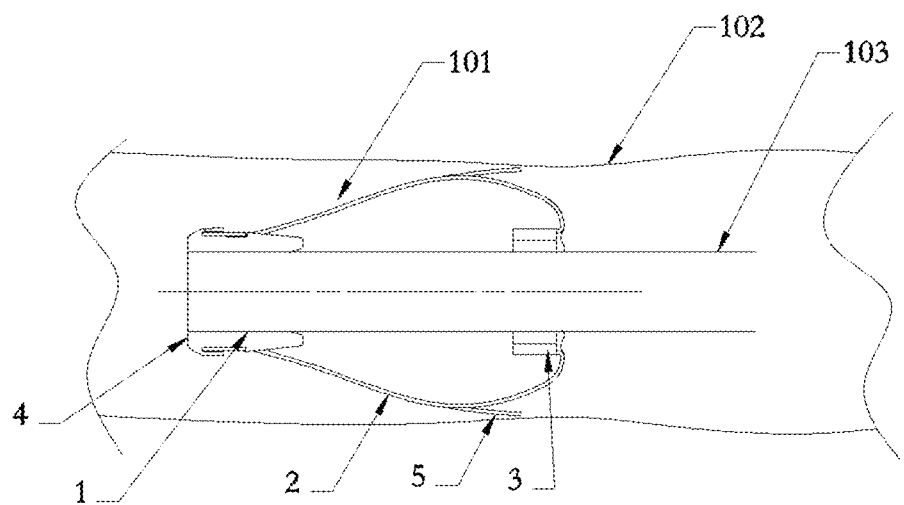
FIG. 2A is a schematic view of the endoscopic end cap during insertion of the endoscope.

As shown in FIG. 2A, when the endoscope is inserted into the human body, i.e., during the insertion of the endoscope, it is pressed by the intestinal tract and others, such that the projecting element 2 is attached to the endoscopic shaft 103, and the movable sleeve 3 is moved proximally in the axial direction of the endoscope. The projecting element 2 is gradually moved closer to the endoscope or even attached closely to the outer surface of the shaft of the endoscope, so that the endoscopic end cap 101 constituted by the sleeve member 1, the projecting element 2, and the movable sleeve 3 forms a substantially smooth and non-angular cylindrical-like structure in a direction parallel to the axial direction of the endoscopic shaft 103. A small resistance is exerted on this structure due to its small radial dimension during insertion of the endoscope, which facilitates introduction of the endoscope into the intestinal tract. Moreover, the portions of the end cap being in contact with the digestive tract are smooth and not angled, thus the intestinal tract will not be scratched, and the injury and pain caused to the patient are reduced.

Figure 2B:
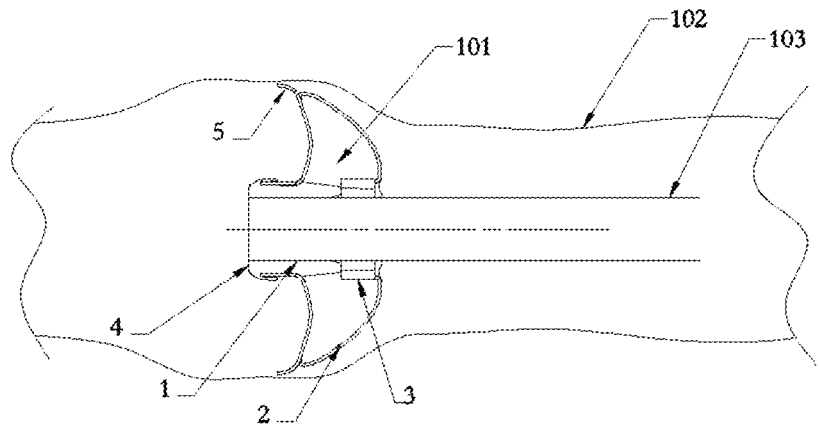
FIG. 2B is a schematic view of the endoscopic end cap during withdrawal of the endoscope.

As shown in FIG. 2B, when the endoscope is being extracted, i.e., withdrawn, from the lumen of the human body, the movable sleeve 3 is pressed by the intestinal tract and is moved distally in the axial direction of the endoscope, so that the projecting element 2 protrudes outward. In this case, a large force (i.e., extraction force) larger than the insertion force is exerted on the endoscopic end cap 101. While the movable sleeve 3 is gradually moving closer to the sleeve member 1, the projecting element 2 is changed from a cylindrical shape to a lantern shape and finally to a pie shape, and the outer perimeter of the projecting element 2 is continuously increased in this process. At this time, the movable sleeve 3 gradually moves toward the direction of the sleeve member 1 until it abuts against the sleeve member 1. When the outer perimeter of the projecting element 2 reaches the maximum value, the projecting element 2 on which a gradually increasing force is exerted will be gradually bent distally, and then the outer perimeter of the projecting element 2 gradually decreases. During the withdrawal of the endoscope, the intestinal tract is supported and dilated by the projecting element 2, whereby the range of the field of view of the endoscope is enlarged, and the accuracy rate of endoscopy is improved. Furthermore, in the withdrawal of the endoscope, the movable sleeve 3 abuts against the sleeve member 1, and the two ends of the projecting element 2 are connected to these two components, respectively, thus these two components provide a good support for the projecting element, so that the endoscopic end cap 101 supports the intestinal tract more strongly, so as to greatly enlarge the field of view of the endoscope. In this way, the endoscopist can directly observe some adenomas in hidden positions without spending more time focusing on the examination of a certain hidden area, whereby the colonoscopy is performed with an improved quality, and the time for examination accompanied by endoscope withdrawal is shortened. It is only necessary for the endoscopist to inject a small amount of gas to assist in the examination, which reduces operational risks and time costs, reduces the patient's pain, and also helps the patient recover as soon as possible.

The endoscopic end cap 101 of the present disclosure may be integrally molded from silicone, rubber, or plastic at one time, and the components are highly manufacturable with low cost. Here, the projecting element 2 may also be woven from a wire of a memory alloy such as nickel-titanium. In this case, the projecting element has a stronger effect of straightening and flattening the intussusception and the curved parts of the intestinal tract, so that adenomas hidden in the intussusception or behind folds can be effectively exposed to the lenses of the colonoscope, and thereby the quality of colonoscopy can be significantly improved.

As shown in FIG. 1, the endoscopic end cap 101 of the present disclosure may further comprise an end cap cover 4. The end cap cover 4 is assembled with the sleeve member 1 and then assembled onto the endoscopic shaft 103. The end cap cover 4 serves the function of further limiting the position of the endoscopic end cap 101 and is fixed to the endoscopic shaft 103, so that slippage of the endoscopic end cap 101 from the endoscopic shaft can be better prevented during insertion or withdrawal of the endoscope. The movable sleeve 3 has an inner diameter slightly larger than the inner diameter of the sleeve member 1 to ensure its free movement in the axial direction around the periphery of the endoscopic shaft 103.

The end cap cover 4 may be made of a material with good transparency, so as not to affect the visibility and field of view of the endoscope.

In the case where there is no end cap cover 4, when a large friction force is exerted on the endoscopic end cap 101 during withdrawal of the endoscope, the movable sleeve 3 will abut against the tubular member (sleeve member) 1 and apply to the sleeve member 1 a force toward the distal direction. At the same time, the projecting element 2 on which the force is exerted will tend to be bent distally, and at this time the sleeve member 1 serves to support the projecting element 2. In other words, the force toward the distal direction exerted on the projecting element 2 will be partially applied to the tubular member 1. The tubular member 1 is connected to the endoscopic shaft 103 in such a manner that it is expanded to cover the distal end of the endoscopic shaft 103. In this connection manner, there may be a risk of slippage of the sleeve member from the endoscopic shaft when a large force is exerted thereon.

If the end cap cover 4 is assembled together with the sleeve member 1 and then connected to the endoscopic shaft 103, the end cap cover 4 will firmly fix the sleeve member 1 to the distal end of the endoscope, so that the possibility of slippage of the endoscopic end cap from the endoscope is further reduced without affecting the existing functions of the endoscopic end cap 101.

Figure 21:
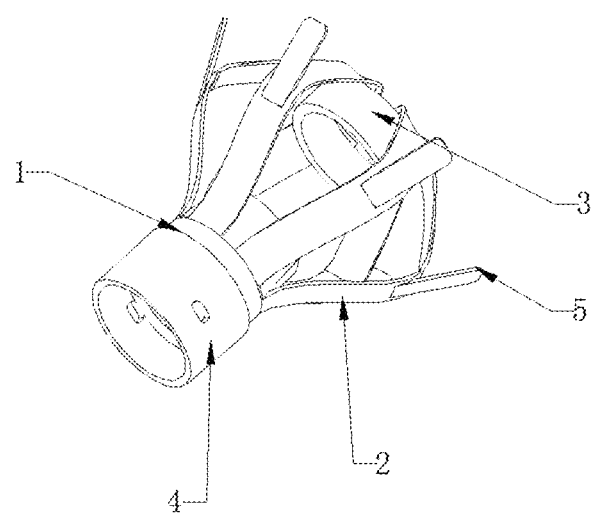
FIG. 21 is a right side view of an eversible endoscopic end cap with an end cap cover comprising a protrusion.
Figures 22A, 22B:
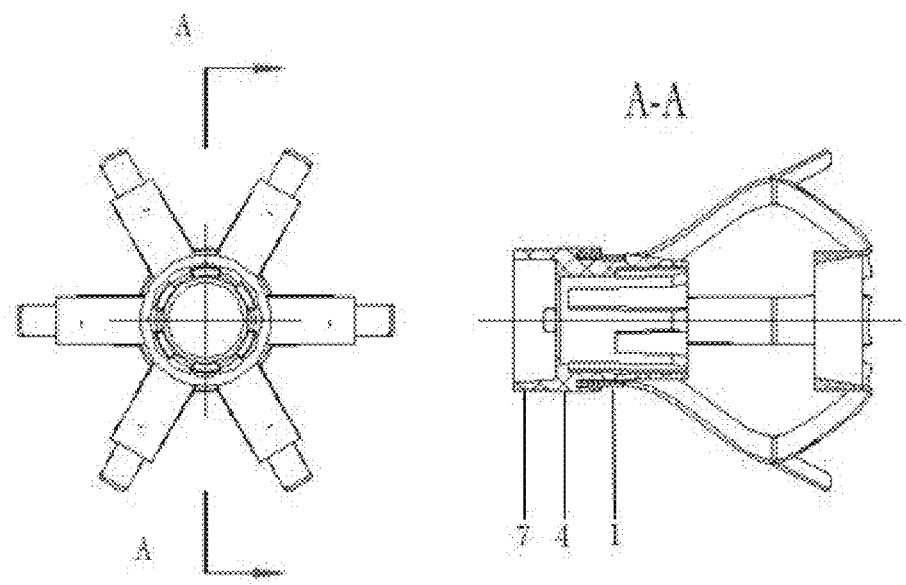
FIG. 22A is a front view of the eversible endoscopic end cap shown in FIG. 21.
FIG. 22B is a sectional view of the eversible endoscopic end cap shown in FIG. 21.

The end cap cover 4 may also be extended distally in the axial direction to form a protrusion, so that its end is located deeper into a part of the human body than the end of the endoscope. The protrusion is higher than the end face of the endoscope. Because the entire end cap cover is made of a highly transparent material, the field of view of the endoscope will not be obstructed during endoscopy. During the examination, the protruding portion may be in direct contact with a lesion, and may separate the obstructions such as folds in the intestinal tract. Moreover, there is a certain distance between the protrusion and the lens, therefore imaging by the lens will not be affected, and also the lesion structure can be observed more easily, and thereby the disease condition can be diagnosed more effectively. The protrusion may be in a cylindrical structure as shown in FIGS. 21, 22A, and 22B; or the protrusion may be conical. Compared to the cylindrical protrusion, the conical protrusion is applicable to more different occasions, such as a surgery that requires tunneling, or a wound with a small opening, where the conical shape facilitates more effective penetration.

Figure 3:
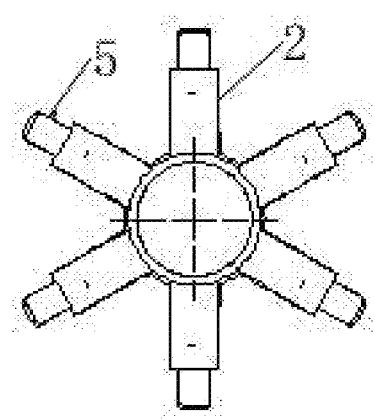
FIG. 3 is a right side view of an eversible endoscopic end cap.
Figure 4A:
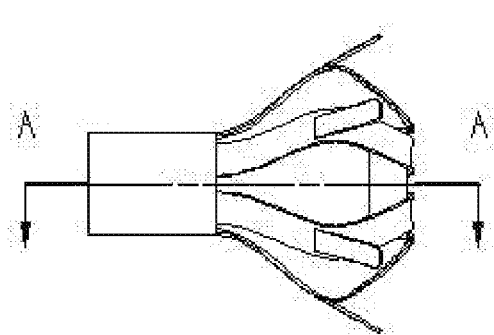
FIG. 4A is a front view of the eversible endoscopic end cap shown in FIG. 3.
Figure 4B:
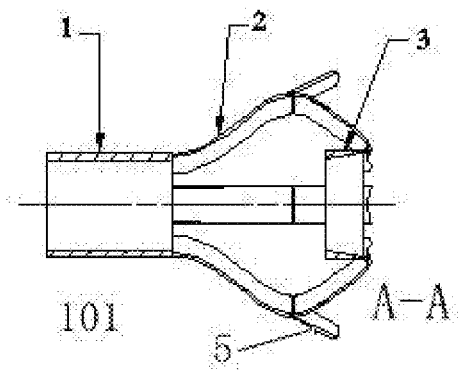
FIG. 4B is a sectional view of the eversible endoscopic end cap shown in FIG. 3.
Figure 5:
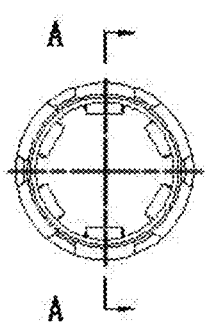
FIG. 5 is a side view of an eversible endoscopic end cap in a state of being extruded from a mold.
Figure 6:
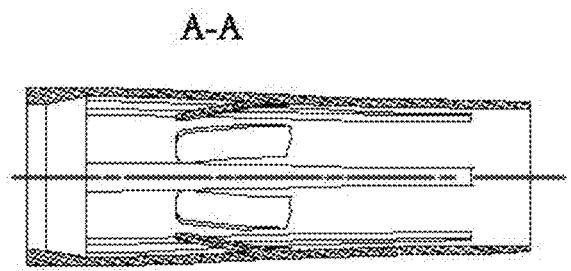
FIG. 6 is a sectional view of the eversible endoscopic end cap in a state of being extruded from a mold.

In an embodiment, FIG. 3 shows a right side view of an eversible endoscopic end cap, comprising a sleeve member 1, a projecting element 2, and a movable sleeve 3. FIGS. 4A and 4B are a front view and a sectional view of the eversible endoscopic end cap, respectively. FIGS. 5 and 6 are a right side view and a sectional view of an eversible endoscopic end cap in a state of being extruded from a mold, respectively, which is in a cylindrical structure as a whole with a larger inner diameter at the left end than at the right end. When the right end is everted and then pulled leftward until it passes over the left end, a configuration as shown in FIGS. 4A and 4B may be formed. In this embodiment, the entire end cap is manufactured by the process shown in FIGS. 5 and 6 to be in an integrally molded structure comprising a projecting element 2 connected to the proximal end of the sleeve member 1. The projecting element 2 comprises a number of elongated structures with a certain width. Each of the elongated structures extends in the axial direction of the end cap from a connection with the sleeve member 1 to a connection with the movable sleeve 3, and the elongated structure may have a consistent, or gradually varying width. Further, the elongated structures of the projecting element 2 may further comprise elongated fins 5. The elongated fins 5 are bent toward the direction of the movable sleeve 3 in the initial state of the manufactured endoscopic end cap 101 and during insertion of an endoscope. During withdrawal of the endoscope, the elongated fins 5 are gradually bent toward the direction of the sleeve member 1 and a ring shape is formed around the sleeve member 1. With the elastic force of the everted fins 5, the lumen of the human body can be supported and dilated or an inner wall of a natural lumen can be opened, and the back portion of the folded wall of the intestinal tract can be dragged out and visualized within the field of view of the endoscope, whereby the detection rate in endoscopy will be greatly increased.

When an endoscope, with the eversible endoscopic end cap 101 in this embodiment, is inserted into a human body for endoscopy, the movable sleeve 3 moves proximally in the axial direction of the endoscope. As the movable sleeve 3 moves proximally, the projecting element 2 with or without elongated fins 5 may be driven to move closer to the direction of the endoscopic shaft 103, so that the endoscopic end cap 101 is gradually moved closer to the endoscope or even attached closely to the outer surface of the endoscopic shaft, and the endoscopic end cap 101 constituted by the sleeve member 1, the projecting element 2, and the movable sleeve 3 forms a substantially smooth and non-angular cylindrical-like structure in a direction parallel to the axial direction of the endoscopic shaft 103. A small resistance is exerted on this structure during insertion of the endoscope, which facilitates introduction of the endoscope into the intestinal tract and further reduces the patient's discomfort.

When the endoscope is being extracted, i.e., withdrawn, from the human body, the movable sleeve 3 is pressed by the intestinal tract and is moved distally in the axial direction of the endoscope. While the movable sleeve 3 is gradually moving closer to the sleeve member 1, the projecting element 2 is changed from a cylindrical shape to a lantern shape and finally to a pie shape, and the outer perimeter of the projecting element 2 is continuously increased in this process. At this time, the movable sleeve 3 gradually moves toward the direction of the sleeve member 1 until it abuts against the sleeve member 1. When the outer perimeter of the projecting element 2 reaches the maximum value, the projecting element 2 on which a gradually increasing force is exerted will be gradually bent distally, and then the outer perimeter of the projecting element 2 gradually decreases. During the extraction of the endoscope, the elongated fins 5 are gradually bent toward the direction of the sleeve member 1, and the fins 5 are attached closely to the intestinal lumen and further generate a supporting force to dilate the intestinal lumen, so that the intussusception and the curved parts of the intestinal tract can be straightened and flattened, and thereby adenomas hidden in the intussusception or behind the folds are exposed to the lenses of the colonoscope. As a result, the surface area of the intestinal lumen observable by the lenses is enlarged, the rate of undetected cases is reduced, and the quality of the colonoscopy is improved.

The end cap is used in cooperation with an endoscope. During withdrawal of the endoscope, the intestinal tract is supported and dilated by the projecting element 2, whereby the range of the field of view of the endoscope is enlarged, and the accuracy rate of endoscopy is improved. Furthermore, the movable sleeve 3 abuts against the sleeve member 1, and the two ends of the projecting element 2 are connected to these two components, respectively, thus these two components provide a good support for the projecting element 2, so that the endoscopic end cap 101 supports the intestinal tract more strongly, so as to greatly enlarge the field of view of the endoscope. In this way, the endoscopist can directly observe some adenomas in hidden positions without spending more time focusing on the examination of a certain hidden area, whereby the colonoscopy is performed with an improved quality, and the time for examination accompanied by endoscope withdrawal is shortened. It is only necessary for the endoscopist to inject a small amount of gas to assist in the examination, which reduces operational risks and time costs, and also contributes to shortening the time for examination accompanied by endoscope withdrawal and reducing the patient's discomfort. Moreover, the endoscopic end cap 101 is made by a simple mold, and the components are highly manufacturable with low cost. The produced endoscopic end cap 101 is everted to provide an enhanced supporting force and achieve a better supporting effect.

Figure 7:
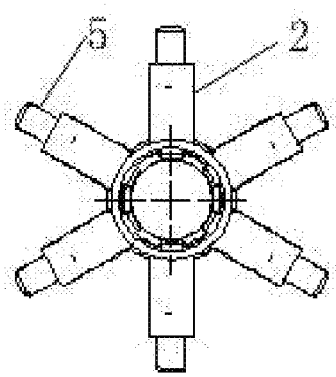
FIG. 7 is a right side view of a combined eversible endoscopic end cap.
Figure 8A:
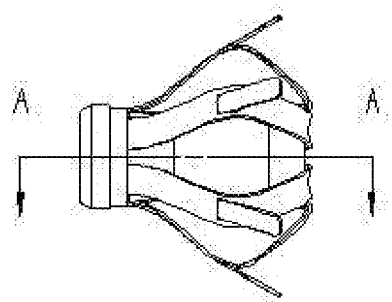
FIG. 8A is a front view of the combined eversible endoscopic end cap shown in FIG. 7.
Figure 8B:
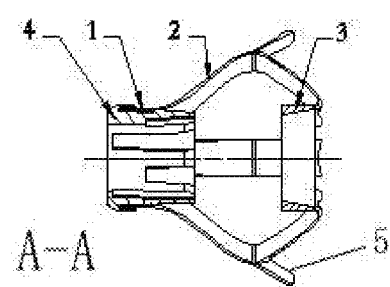
FIG. 8B is a sectional view of the combined eversible endoscopic end cap shown in FIG. 7.

The endoscopic end cap 101 may also be used in combination with the end cap cover 4. FIGS. 7, 8A, and 8B show a side view, a front view, and a sectional view of a combined eversible endoscopic end cap, wherein the sleeve member 1 is combined with the end cap cover 4 and then assembled onto the endoscopic shaft. The end cap cover 4 serves the function of further limiting the position of the endoscopic end cap 101 and is fixed to the endoscope to prevent slippage of the end cap from the endoscope during insertion or withdrawal of the endoscope. The movable sleeve 3 has an inner diameter slightly larger than the inner diameter of the sleeve member 1, so as to ensure its free forward or backward movement in the axial direction around the periphery of the endoscopic shaft.

Figure 9:
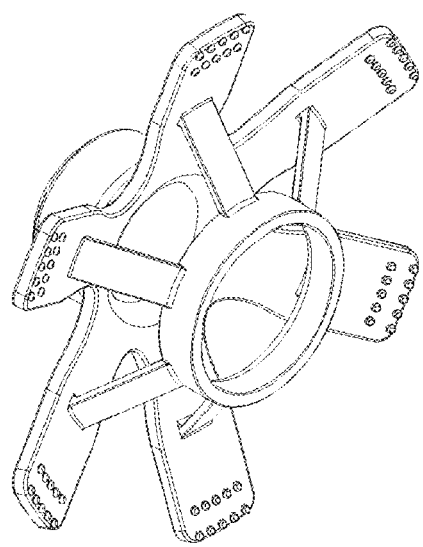
FIG. 9 is a schematic view of an umbrella-type endoscopic end cap.
Figure 10:
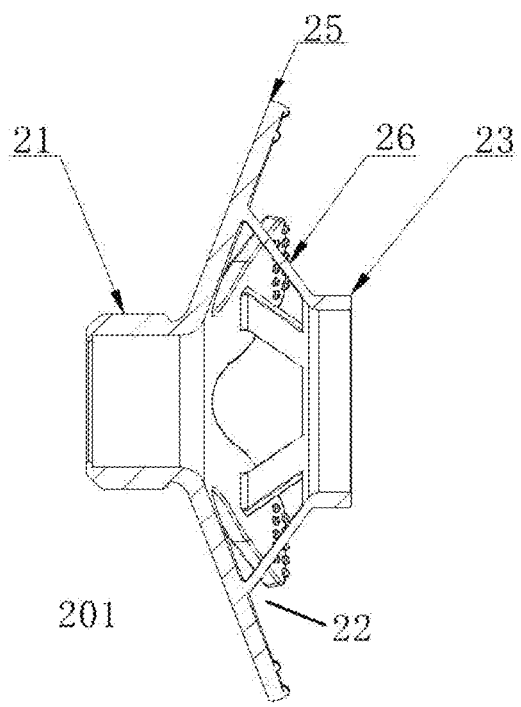
FIG. 10 is a sectional view of the umbrella-type endoscopic end cap shown in FIG. 9.
Figure 11A:
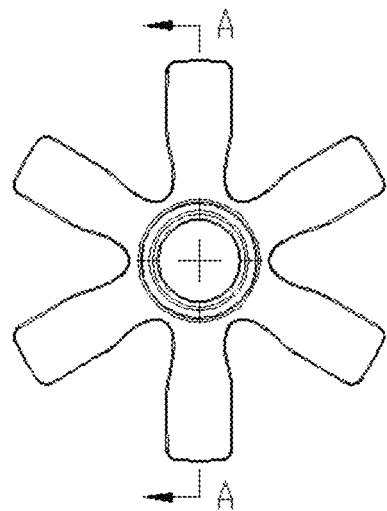
FIGS. 11A and 11B are left and right side views of the umbrella-type endoscopic end cap shown in FIG. 9, respectively.
Figure 11B:
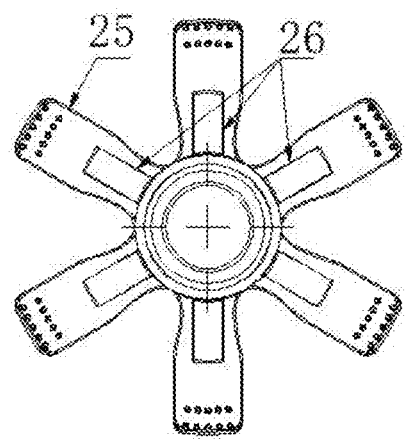
Figure 12A:
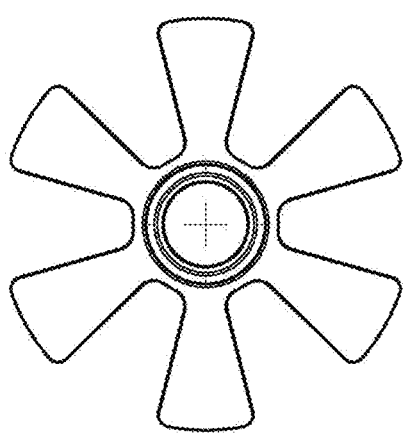
FIGS. 12A and 12B are left and right side views of another umbrella-type endoscopic end cap, respectively.
Figure 12B:
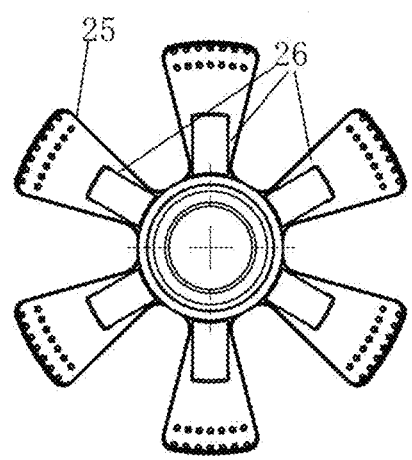

FIGS. 9 to 12 show another embodiment of the present disclosure. FIGS. 9, 10, and 11 show an umbrella-type endoscopic end cap, and FIG. 12 shows another umbrella-type endoscopic end cap, wherein FIG. 9 is a schematic view of an umbrella-type endoscopic end cap, FIG. 10 is a front view of the umbrella-type endoscopic end cap shown in FIG. 9, FIG. 11 shows left and right side views of the umbrella-type endoscopic end cap shown in FIG. 9, and FIG. 12 shows left and right side views of another umbrella-type endoscopic end cap. The umbrella-type endoscopic end cap 201 comprises a sleeve member 21, a projecting element 22, and a movable sleeve 23. The projecting element comprises umbrella-shaped projecting elements 25 and connecting rods 26. The umbrella-shaped projecting element 25 extends in the axial direction from a connection to the sleeve member 21, one end of the connecting rod 26 is connected to one end of the movable sleeve 23, and the other end of the connecting rod 26 is connected to the axially extending end of the umbrella-shaped projecting element 25, so that an umbrella-like structure is formed by the sleeve member 21, the projecting element 22, and the movable sleeve 23.

The umbrella-shaped projecting element 25 of the umbrella-type endoscopic end cap 201 may be in a rectangular shape with the same width in the direction where it extends outwardly from the connection to the sleeve member 21, as shown in FIG. 11, or may be in a trapezoidal structure with a width gradually widening in the direction where it extends outwardly from the connection to the sleeve member 21, as shown in FIG. 12.

A number of projections may be provided at the end of the umbrella-shaped projecting element to increase the friction force. The projections may be designed with corresponding shapes according to working requirements, and may be point-shaped projections, crossed diamond-shaped projections, or the like.

When the endoscope is inserted into a human body for endoscopy, the movable sleeve 23 moves proximally in the axial direction of the endoscope. As the movable sleeve 23 moves proximally, the projecting element 22 may be driven to move closer to the direction of the endoscopic shaft 103, so that the endoscopic end cap 201 is gradually moved closer to the endoscope or even attached closely to the outer surface of the shaft of the endoscope, and the endoscopic end cap 201 constituted by the sleeve member 21, the projecting element 22, and the movable sleeve 23 forms a substantially smooth and non-angular cylindrical-like structure in a direction parallel to the axial direction of the endoscopic shaft 103. A small resistance is exerted on this structure during insertion of the endoscope, which facilitates introduction of the endoscope into the intestinal tract and further reduces the patient's discomfort.

When the endoscope is being extracted, i.e., withdrawn, from the human body, the movable sleeve 23 is pressed by the intestinal tract and is moved distally in the axial direction of the endoscope, the connecting rods 26 are opened, and the umbrella-shaped projecting elements 25 are driven to be completely dilated to form an umbrella shape, so that the inner wall of the digestive tract of the patient can be dilated during the withdrawal of the endoscope, and a lesion(s) at the fold(s) behind the inner wall can be dragged out and visualized within the field of view of the endoscope, which enlarges the range of the field of view of the endoscope and hence increases the endoscopic detection rate. At this time, the movable sleeve 23 is forced to move to abut against the sleeve member, and the umbrella-shaped projecting elements 25 have the maximum outer perimeter when they are perpendicular to the sleeve member. Thereafter, as the exerted force (i.e., extraction force) increases, the umbrella-shaped projecting elements will hardly be bent distally under the action of the connecting rods, and only the end portions thereof may possibly be bent distally. At this time, the outer perimeter of the projecting element will decrease slightly and then no longer change with the increase of the extraction force. The extraction force exerted during examination accompanied by endoscope withdrawal is greater than the insertion force exerted during insertion of the endoscope.

The end cap is used in cooperation with an endoscope. During withdrawal of the endoscope, the intestinal tract is supported and dilated by the projecting element 22, whereby the range of the field of view of the endoscope is enlarged, and the accuracy rate of endoscopy is improved. Furthermore, the movable sleeve 23 abuts against the sleeve member 21, and the two ends of the projecting element 22 are connected to these two components, respectively, thus these two components provide a good support for the projecting element 22, so that the endoscopic end cap 201 supports the intestinal tract more strongly, so as to greatly enlarge the field of view of the endoscope. In this way, the endoscopist can directly observe some adenomas in hidden positions without spending more time focusing on the examination of a certain hidden area, whereby the colonoscopy is performed with an improved quality, and the time for examination accompanied by endoscope withdrawal is shortened. It is only necessary for the endoscopist to inject a small amount of gas to assist in the examination, which reduces operational risks and time costs, and also contributes to shortening the time for examination accompanied by endoscope withdrawal and reducing the patient's discomfort.

The endoscopic end cap 201 may also be used in combination with the end cap cover 24, wherein the sleeve member 21 is combined with the end cap cover 24 and then assembled onto the endoscopic shaft. The end cap cover 24 serves the function of further limiting the position of the endoscopic end cap 201 and is fixed to the endoscope to prevent slippage of the end cap from the endoscopic shaft during insertion or withdrawal of the endoscope. The movable sleeve 23 has an inner diameter slightly larger than the inner diameter of the sleeve member 21 to ensure its free forward or backward movement in the axial direction around the periphery of the endoscopic shaft.

Figure 15:
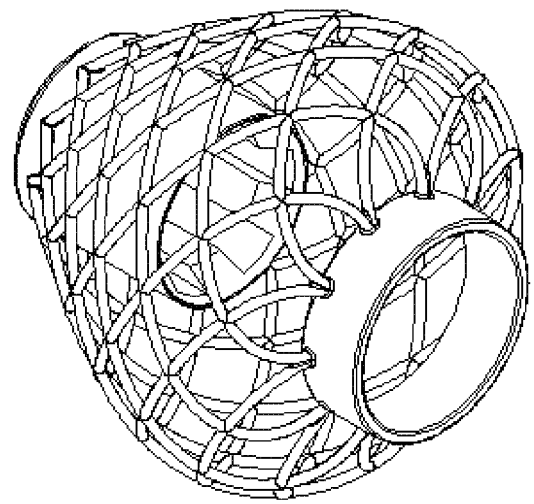
FIG. 15 is a schematic view of another mesh-type endoscopic end cap.
Figure 16A:
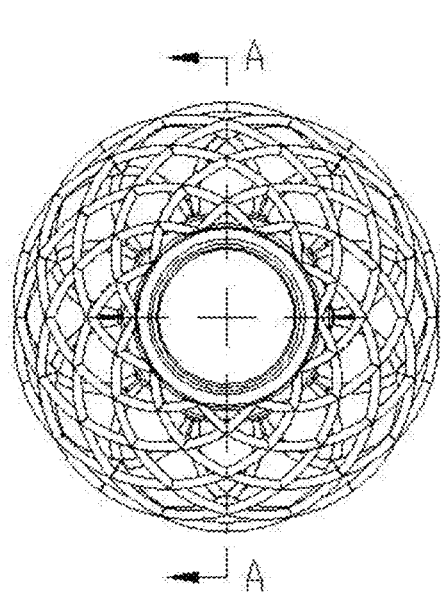
FIGS. 16A and 16B are a left side view and a front view of the endoscopic end cap shown in FIG. 15, respectively.
Figure 16B:
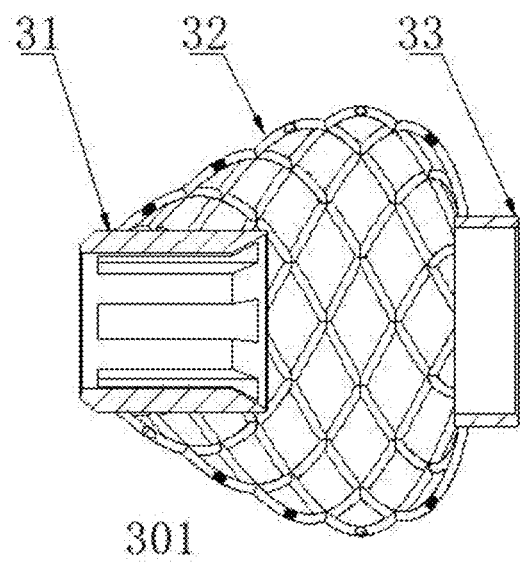
Figure 17:
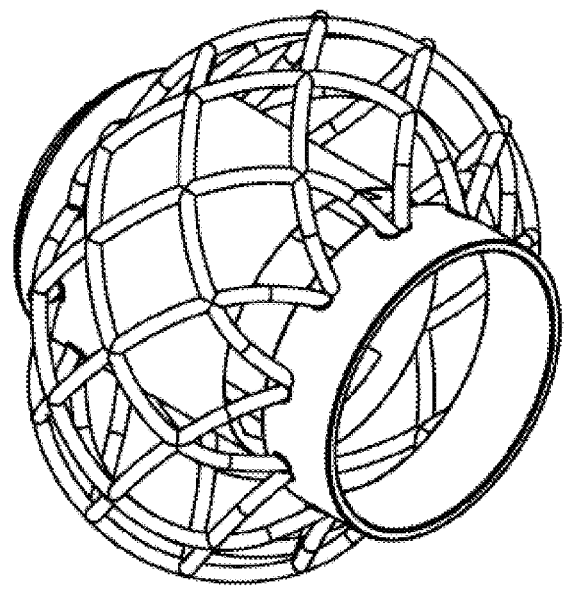
FIG. 17 is a schematic view of another mesh-type endoscopic end cap.
Figure 18A:
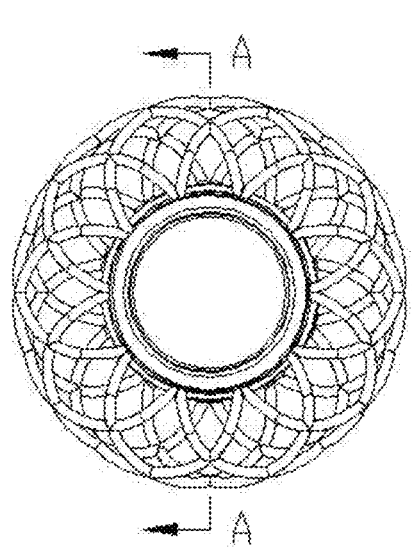
FIGS. 18A and 18B are a left side view and a front view of the mesh-type end cap shown in FIG. 17, respectively.
Figure 18B:
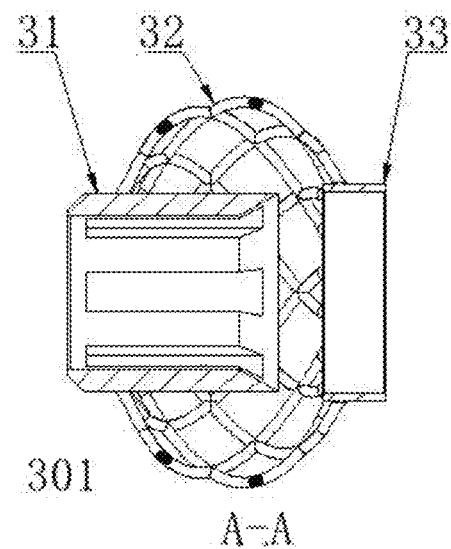

Another embodiment is now given with reference to FIGS. 13 to 20. FIGS. 13 to 16 show mesh-type endoscopic end cap, FIGS. 17 and 18 show another mesh-type endoscopic end cap, and FIGS. 19 and 20 are schematic views of a mesh-type end cap assembled with an end cap cover.

Figure 13:
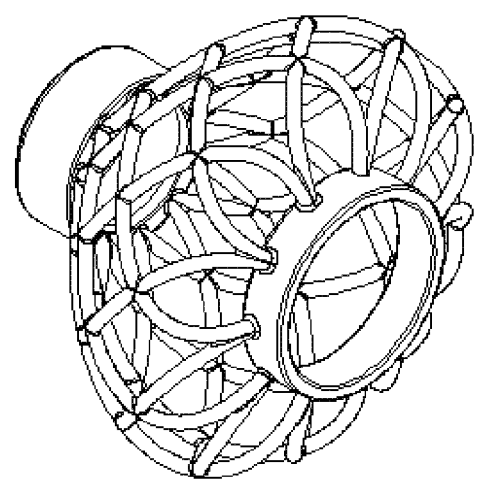
FIG. 13 is a schematic view of a mesh-type endoscopic end cap.
Figures 14A, 14B:
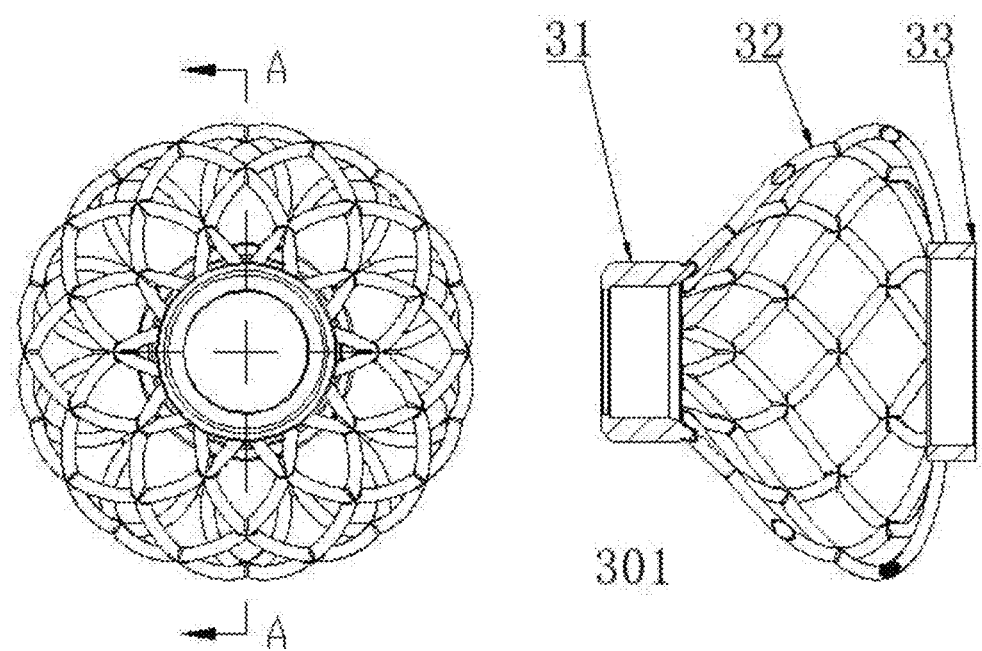
FIGS. 14A and 14B are a left side view and a front view of the mesh-type endoscopic end cap shown in FIG. 13, respectively.

FIGS. 13 and 15 are schematic views of mesh-type endoscopic end cap, FIG. 14 shows a left side view and a front view of the mesh-type endoscopic end cap corresponding to FIG. 13, and FIG. 16 shows a left side view and a front view of the mesh-type endoscopic end cap corresponding to FIG. 15.

The structure of the mesh-type endoscopic end cap 301 comprises a sleeve member 31, a projecting element 32, and a movable sleeve 33 in this order from the distal end to the proximal end. The projecting element may be a meshed projecting element. The meshed projecting element 32 may be integrally formed by means of weaving, and is connected at one end thereof to one end of the sleeve member 31 and connected at the other end thereof to one end of the movable sleeve 33.

The meshed projecting element 32 may be connected to different positions of the sleeve member 31. Specifically, the meshed projecting element 32 may be connected to the proximal end of the sleeve member 31, or the meshed projecting element 32 may be connected to the distal end of the sleeve member 31, so that the sleeve member 31 may be wrapped or half-wrapped in the meshed projecting element 31. When the mesh-type endoscopic end cap 301 is being introduced into a human body along with the endoscope, the endoscopic end cap 301 with the meshed projecting element 32 connected to the proximal end of the sleeve member 31 is more easily introduced into the human body.

FIG. 17 is a schematic view of another mesh-type endoscopic end cap, and FIG. 18 shows a top view and a front view of the endoscopic end cap of FIG. 17. The lantern-type endoscopic end cap is different from the mesh-type endoscopic end cap shown in FIGS. 13 to 16 in that the sleeve member has a longer axial length and the projecting element is connected to the distal end of the sleeve member. Therefore, the sleeve member of the lantern-type endoscopic end cap can be more stably fixed to the endoscope than the sleeve member of the strawberry-type end cap, and can provide a greater supporting force to the meshed projecting element, so that it is kept in the dilated state and not easily deformed.

It should be noted that in the mesh-type endoscopic end cap here, the meshed projecting element thereof when dilated may be in the shape of a lantern, a strawberry, a water droplet, a polygon, a circle, a mushroom, a cup, a sphere, a trumpet, a triangle, a meshed shape with wings, or the like.

FIG. 19 is a schematic view of a mesh-type endoscopic end cap combined with an end cap cover, and FIG. 20 shows a left side view and a front view of the mesh-type endoscopic end cap combined with an end cap cover shown in FIG. 19. The mesh-type endoscopic end cap combined with an end cap cover comprises a sleeve member 31, a meshed projecting element 32, a movable sleeve 33, and an end cap cover 34.

The combined endoscopic end cap, in which the sleeve member 31 is bonded and combined with the end cap cover 34 and then assembled to the end of the endoscope, can be more firmly fixed to the endoscope than the case where there is no end cap cover 34, so that the end cap 301 is much less likely to slip off from the endoscope, and thus the endoscopic end cap can achieve a better effect.

When the endoscope is inserted into a human body for endoscopy, the movable sleeve 33 moves proximally in the axial direction of the endoscope. As the movable sleeve 33 moves proximally, the projecting element 32 may be driven to move closer to the direction of the endoscopic shaft 103, so that the endoscopic end cap 301 is gradually moved closer to the endoscope or even attached closely to the outer surface of the shaft of the endoscope, and the endoscopic end cap 301 constituted by the sleeve member 31, the projecting element 32, and the movable sleeve 33 forms a substantially smooth and non-angular cylindrical-like structure in a direction parallel to the axial direction of the endoscopic shaft 103. A small resistance is exerted on this structure during insertion of the endoscope, which facilitates introduction of the endoscope into the intestinal tract. Moreover, the mesh-type endoscopic end cap has a projecting element being in contact with the digestive tract at a smaller area and is correspondingly subjected to less resistance and further reduces the patient's discomfort than the eversible and umbrella-type endoscopic end caps.

When the endoscope is being extracted, i.e., withdrawn, from the human body, the movable sleeve 33 is pressed by the intestinal tract and is moved distally in the axial direction of the endoscope, and the projecting element 32 is contracted distally as a support, so that the inner wall of the digestive tract of the patient can be dilated during the withdrawal of the endoscope. Since the dilated projecting element 32 has a large number of mesh gaps, some tissues will be squeezed into the mesh gaps due to limited space during the withdrawal of the endoscope, so that lesions at the folds behind the inner wall will be gradually dragged out and visualized within the field of view of the endoscope while the endoscope is being withdrawn, which enlarges the range of the field of view of the endoscope and hence increases the endoscopic detection rate.

As the movable sleeve 33 is forced to move to abut against the sleeve member, the projecting element 32 is changed from a cylindrical-like shape when inserted to a spherical-like shape and then to a pie shape. In this process, the outer perimeter of the projecting element becomes larger as an increasing force is exerted thereon. Thereafter, as the exerted force continuously increases, the outermost side of the pie-shaped projecting element will be gradually bent toward the distal end of the endoscope. In this process, the outer perimeter of the projecting element decreases as the exerted force increases. The extraction force exerted during examination accompanied by endoscope withdrawal is greater than the insertion force exerted during insertion of the endoscope.

The end cap is used in cooperation with an endoscope. During withdrawal of the endoscope, the intestinal tract is supported and dilated by the projecting element 32, whereby the range of the field of view of the endoscope is enlarged, and the accuracy rate of endoscopy is improved. Furthermore, the movable sleeve 33 abuts against the sleeve member 31, and the two ends of the projecting element 32 are connected to these two components, respectively, thus these two components provide a good support for the projecting element 32, so that the endoscopic end cap 301 supports the intestinal tract more strongly, so as to greatly enlarge the field of view of the endoscope. In this way, the endoscopist can directly observe some adenomas in hidden positions without spending more time focusing on the examination of a certain hidden area, whereby the colonoscopy is performed with an improved quality, and the time for examination accompanied by endoscope withdrawal is shortened. It is only necessary for the endoscopist to inject a small amount of gas to assist in the examination, which reduces operational risks and time costs, and also contributes to shortening the time for examination accompanied by endoscope withdrawal and reducing the patient's discomfort.

What is claimed is:

1. An endoscopic end cap, capable of being arranged at a distal end of an endoscopic shaft and comprising: a sleeve member, a projecting element, and a movable sleeve, wherein the projecting element has one end connected to the sleeve member and another end connected to the movable sleeve, wherein when an endoscope provided with the endoscopic end cap is withdrawn, the movable sleeve moves toward the distal end of the endoscopic shaft until it abuts against the sleeve member, so as to provide a supporting force for the projecting element, so that the projecting element is dilated so as to enlarge a field of view of the endoscope, wherein the projecting element comprises umbrella-shaped projecting elements and connecting rods, and wherein when the endoscope is withdrawn, the movable sleeve moves towards a distal end in an axial direction of the endoscope, and only end portions of the umbrella-shaped projecting elements are bent toward a distal end under an action of the connecting rods.

2. The endoscopic end cap according to claim 1, wherein when the endoscope provided with the endoscopic end cap is inserted, the movable sleeve moves proximally in an axial direction of the endoscope, and the projecting element is gradually moved closer to the endoscope, so that the endoscopic end cap, constituted by the sleeve member, the projecting element and the movable sleeve, forms a substantially smooth and non-angular cylindrical-like structure in a direction parallel to the endoscopic shaft.

3. The endoscopic end cap according to claim 2, wherein the end cap is integrally molded from silicone, rubber, or plastic, and alternatively, the projecting element is woven from a wire of nickel-titanium memory alloy.

4. The endoscopic end cap according to claim 2, further comprising an end cap cover, wherein the end cap cover is assembled with the sleeve member and then assembled onto the endoscopic shaft.

5. The endoscopic end cap according to claim 1, wherein the sleeve member has an inner diameter smaller than a diameter of the endoscopic shaft.

6. The endoscopic end cap according to claim 1, wherein the movable sleeve has an inner diameter slightly larger than that of the sleeve member.

7. The endoscopic end cap according to claim 1, wherein the end cap is integrally molded from silicone, rubber, or plastic, and alternatively, the projecting element is woven from a wire of nickel-titanium memory alloy.

8. The endoscopic end cap according to claim 1, further comprising an end cap cover, wherein the end cap cover is assembled with the sleeve member and then assembled onto the endoscopic shaft.

9. The endoscopic end cap according to claim 8, wherein the end cap cover is made of a transparent material.

10. The endoscopic end cap according to claim 8, wherein the end cap cover further comprises a protrusion, wherein the protrusion is cylindrical or conical.

11. The endoscopic end cap according to claim 1, wherein each of the umbrella-shaped projecting elements, at its end, has several projections.

12. The endoscopic end cap according to claim 1, wherein the sleeve member is in a shape of circle, ellipse, triangle, cone or polygon.

* * * * *